United States Patent [19]

Zupan

[11] 4,338,455

[45] Jul. 6, 1982

[54] NOVEL PROCESS AND INTERMEDIATES USEFUL IN THE PREPARATION OF SYMPATHOMIMETIC AMINES

[75] Inventor: Jacob A. Zupan, Lawrence, Kans.

[73] Assignee: Merck & Co., Inc., Rahway, N.J.

[21] Appl. No.: 233,457

[22] Filed: Feb. 11, 1981

[51] Int. Cl.$^3$ .......................................... C07C 125/065
[52] U.S. Cl. ......................................... 560/29; 560/27; 560/28; 546/263; 546/314; 546/318; 546/322; 546/326; 260/404; 260/404.5; 260/405.5
[58] Field of Search ............................. 560/27, 29, 28; 546/263, 314, 318, 322, 326; 260/404, 404.5, 405.5

[56] References Cited

U.S. PATENT DOCUMENTS

| | | | |
|---|---|---|---|
| 3,843,796 | 10/1974 | Miller | 424/273 |
| 3,859,331 | 1/1975 | Kaiser et al. | 560/29 |
| 3,875,207 | 4/1975 | Iselin et al. | 560/29 |
| 4,041,076 | 8/1977 | Avenia et al. | 560/29 |

FOREIGN PATENT DOCUMENTS

2153801  3/1972  Fed. Rep. of Germany ........ 560/29

OTHER PUBLICATIONS

Walker et al., J. Pharm. Sci., 67, No. 4, 558–559, 1978.

*Primary Examiner*—G. T. Breitenstein
*Attorney, Agent, or Firm*—Michael C. Sudol, Jr.; Mario A. Monaco

[57] ABSTRACT

The invention relates to a novel process and novel intermediates useful in the preparation of sympathomimetic amines. The pharmacologically useful final products, which are acyl derivatives of mono- and dihydroxy aromatic amines (e.g., catechol amines) can be prepared in optically active or racemic form by reacting the corresponding mono- or dihydroxy aromatic amine with a reagent capable of forming the N-tert-butoxycarbonyl derivative thereof; reacting the novel intermediate thus obtained with an acyloxymethyl chloride to afford the corresponding novel mono- or diacylated N-protected aromatic amine; and removing the N-protecting group therefrom.

18 Claims, No Drawings

NOVEL PROCESS AND INTERMEDIATES USEFUL IN THE PREPARATION OF SYMPATHOMIMETIC AMINES

BACKGROUND OF THE INVENTION

1. Field of the Invention

The present invention is directed to a novel synthetic process for preparing esters of catechol amines and other sympathomimetic amines in optically active or racemic form, and to novel N-tert-butoxycarbonyl intermediates useful in the subject process.

2. Description of the Prior Art

U.S. Pat. Nos. 3,809,714, 3,825,583, 3,839,584, 3,868,461, 3,959,485, 3,966,749, 3,908,017, 4,035,405, 4,088,783, 4,145,441 and 4,158,005, all in the name of the instant assignee, disclose a number of sympathomimetic amine derivatives within the general formula (I) set forth hereinbelow, and nontoxic pharmaceutically acceptable acid addition salts thereof. The compounds of formula (I) and their salts are useful in the treatment of conditions responsive to sympathomimetic amines, e.g., glaucoma, asthma and nasal congestion.

Prior art methods for the preparation of compounds within the scope of the formula (I) below generally have provided the compound in the form of a racemic mixture, i.e., a mixture containing both the biologically active and the biologically inactive isomer. Normally, the compounds of formula (I) have been administered in the form of a racemic mixture, as the means to separate the optically active, biologically active isomers from their racemic mixtures are tedious and expensive. In fact, resolution of the racemic mixtures of many of the compounds of formula (I) has not been reported in the literature.

Consequently, it is apparent that a need exists for a means of directly synthesizing the optically active, biologically active forms of the compounds of formula (I), thus avoiding the necessity of first obtaining the racemic mixture and then either resolving the racemic mixture and administering the optically and biologically active isomer thereof, or else, as is more frequently the case, administering the racemic mixture itself. In the latter case, it is apparent that the dosage amount of a racemic mixture which would be required to achieve therapeusis would be much greater than that required if only the optically active, biologically active isomer were administered.

SUMMARY OF THE INVENTION

Accordingly, the present invention has as an object a novel process for the preparation of a compound of the general formula

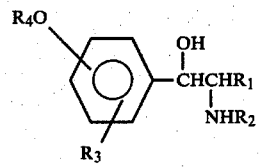
(I)

wherein $R_1$ is H or alkyl of 1 to 7 carbon atoms; $R_2$ is H, alkyl of 1 to 7 carbon atoms, or

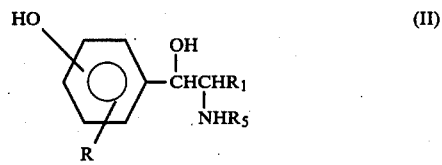

wherein m is zero or one, the alkylene portion contains 1 to 5 carbon atoms, and X is H or $-OR'_4$ wherein $R'_4$ is identical to $R_4$ as defined below; $R_3$ is H, Cl, $-CH_2OH$ or $-OR''_4$ wherein $R''_4$ is identical to $R_4$ as defined as below; and $R_4$ is an acyl radical; or a nontoxic pharmaceutically acceptable acid addition salt thereof; which comprises:

(a) reacting a compound of the general formula

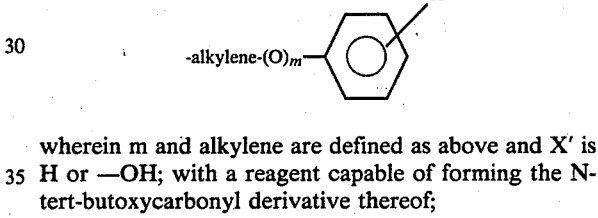
(II)

wherein $R_1$ is defined as above; R is H, Cl, $-CH_2OH$ or $-OH$; and $R_5$ is H, alkyl of 1 to 7 carbon atoms, or

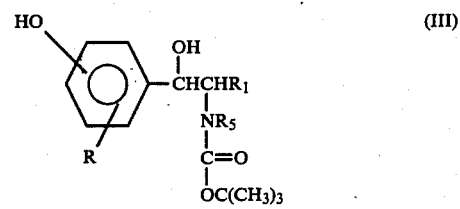

wherein m and alkylene are defined as above and X' is H or $-OH$; with a reagent capable of forming the N-tert-butoxycarbonyl derivative thereof;

(b) reacting the resultant N-tert-butoxycarbonyl derivative of the formula

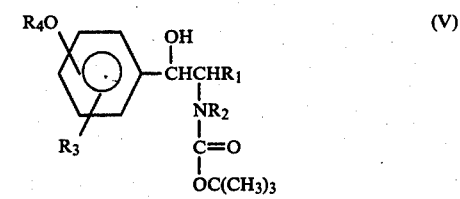
(III)

wherein R, $R_1$ and $R_5$ are defined as above, with an acyloxymethyl chloride of the formula

$R_4OCH_2Cl$ (IV)

wherein $R_4$ is an acyl radical, in an organic solvent in the presence of a base; and (c) removing the tert-butoxycarbonyl protecting group from the resultant compound of the formula (V)

wherein $R_1$, $R_2$, $R_3$, and $R_4$ are defined as above.

The novel process for the preparation of compounds of formula (I) and their nontoxic pharmaceutically acceptable acid addition salts which is set forth above provides the desired compounds in optically active or in racemic form, depending on the particular starting material employed. Said process further provides novel intermediates useful in the preparation of the compounds of formula (I), said novel intermediates having the structural formulas (III) and (V) set forth above.

DETAILED DESCRIPTION OF THE INVENTION

With respect to the various groups encompassed by the generic terms used here and throughout this specification, the following definitions and explanations are applicable:

The alkyl groups encompassed by $R_1$ include straight and branched-chain radicals containing the indicated number of carbon atoms, with methyl and ethyl being preferred.

The alkyl groups encompassed by $R_2$ and $R_5$ likewise can be straight or branched-chain containing the indicated number of carbon atoms. In the case of the $R_2$ and $R_5$ substituents, preferred alkyl groups are methyl, isopropyl and tert-butyl.

When $R_2$ is an

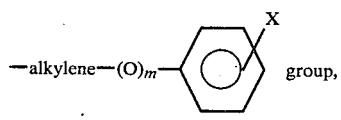 group, or when $R_5$ is an

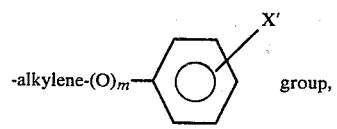 group, the alkylene bridge can be a straight or branched-chain group of the type $C_nH_{2n}$, wherein n is 1 to 5, e.g. ethylene, 1,2-propylene and 1,3-butylene.

With respect to the acyl groups represented by the $R_4$ term, it is to be noted that at each occurrence $R_4$ preferably represents an acyl radical selected from the group consisting of alkanoyl having 1 to 22 carbon atoms, alkenoyl having one or two double bonds and having 4 to 22 carbon atoms;

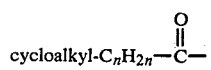

having a total of 4 to 10 carbon atoms of which 3 to 7 are ring carbon atoms in the cycloalkyl portion and wherein n is zero, one or two; phenoxyacetyl; naphthalenecarbonyl; pyridinecarbonyl; and

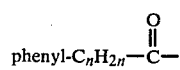

wherein n is zero, one or two and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 1 to 6 atoms.

When $R_4$ is alkanoyl containing 1 to 22 carbon atoms, there are included both unbranched and branched alkanoyl, for example, formyl, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl, docosanyl and 7,7-dimethyloctanoyl. Branched alkanoyl groups are generally preferred, an especially preferred group being pivaloyl.

When $R_4$ is alkenoyl having one or two double bonds and having 4 to 22 carbon atoms, there are included, for example, crotonyl, 9-octadecenoyl, 2,5-hexadienoyl, 3,6-octadienoyl, 10,13-octadecadienoyl and 5,13-docosadienoyl.

When $R_4$ is

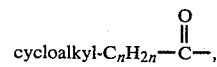

there are included cycloalkanecarbonyl and cycloalkanealkanoyl groups wherein the cycloalkane portion can optionally bear 1 or 2 alkyl groups as substituents, e.g., cyclopropanecarbonyl, 1-methylcyclopropanecarbonyl, cyclopropaneacetyl, alpha-methylcyclopropaneacetyl, 1-methylcyclopropaneacetyl, 2-amylcyclopropaneacetyl, cyclopropanepropionyl, alpha-methylcyclopropanepropionyl, 2-isobutylcyclopropanepropionyl, 2-hexylcyclopropanecarbonyl, cyclobutanepropionyl, 2-methylcyclobutanecarbonyl, 1,3-dimethylcyclobutanecarbonyl, 3,3-dimethylcyclobutanecarbonyl, cyclobutaneacetyl, 2,2-dimethyl-3-ethylcyclobutaneacetyl, cyclobutanepropionyl, cyclopentanecarbonyl, 1-methyl-3-isopropylcyclopentanecarbonyl, cyclopentanepropionyl, cyclohexanecarbonyl, cyclohexaneacetyl, 4-methylcyclohexaneacetyl, cycloheptanecarbonyl, 4-methylcycloheptaneacetyl, and cycloheptanepropionyl.

When $R_4$ is

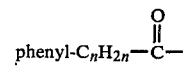

there are included, for example, benzoyl, phenylacetyl, alpha-phenylpropionyl, beta-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, beta-(p-ethylphenyl)propionyl, p-anisoyl, m-anisoyl, o-anisoyl, m-isopropoxybenzoyl, p-n-butoxybenzoyl, 3-methoxy-4-ethoxybenzoyl, 3,4,5-trimethoxybenzoyl, 2,4,6-triethoxybenzoyl, p-methoxyphenylacetyl, m-isobutoxyphenylacetyl, 3,4-diethoxyphenylacetyl, beta-(3,4,5-trimethoxyphenyl)-propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, alpha-(m-bromophenyl)propionyl, p-trifluoromethylbenzoyl, 2,4-di(trifluoromethyl)benzoyl, m-trifluoromethylphenylacetyl, beta-(p-trifluoromethylphenyl)propionyl, 2-methyl-4-methoxybenzoyl, 3-chloro-4-ethoxybenzoyl, beta-(3-methyl-4-chlorophenyl)propionyl, p-dimethylaminobenzoyl, m-diethylaminobenzoyl, p-dibutylaminobenzoyl, p-(N-methyl-N-ethylamino)benzoyl, o-acetamidobenzoyl, m-propionamidobenzoyl, p-hexanoylaminobenzoyl, 3-chloro-4-acetamidophenylacetyl, and p-acetamidophenylpropionyl.

When $R_4$ is naphthalenecarbonyl, there are included 1-naphthalenecarbonyl and 2-naphthalenecarbonyl.

When $R_4$ is pyridinecarbonyl, there are included picolinoyl (2-pyridinecarbonyl), nicotinoyl (3-pyridinecarbonyl), and isonicotinoyl (4-pyridinecarbonyl).

Finally, the term "nontoxic pharmaceutically acceptable acid addition salt" as used herein generally includes the nontoxic acid addition salts of selected compounds of formula (I), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicyclic, sulfanilic, fumaric, sulfonic, toluenesulfonic, and the like.

By selecting the appropriate reactants for the ultimate specie desired, the compounds of formula (I) are conveniently prepared in accordance with the synthetic scheme of the present invention.

The compounds of formula (I) which are prepared by the process of the present invention find therapeutic application in the treatment of warm-blooded animals (e.g., humans) in the management of asthma, as decongestants, vasoconstrictors, mydriatic agents and antiglaucomatous agents, and in the treatment of other conditions responsive to sympathomimetic amines. Upon administration, the compounds of formula (I) will enzymatically "cleave" and release the parent phenol, the therapeutically active moiety thereof. Thus, in a preferred embodiment, the present invention provides a novel process and novel intermediates to acylated derivatives of such known sympathomimetic amines as epinephrine, isoproterenol, norepinephrine, phenylephrine, metaraminol, metaproterenol, terbutaline, nordeferin, colterol, deterenal, albuterol and fenoterol, and the nontoxic pharmaceutically acceptable acid addition salts thereof. The instant process and intermediates are especially preferred when they provide acylated derivatives of the aforementioned sympathomimetic amines wherein the acyl group is alkanoyl as hereinbefore defined, most especially when the alkanoyl group is branched, e.g., pivaloyl. Also, while it is a particular and surprising advantage of the present process that the stereochemical integrity of the starting material of formula (II) can be maintained throughout the instant reaction scheme, thus affording an attractive synthetic route to the optically and biologically active isomers of formula (I), it will be apparent to those skilled in the art that the process of the invention can be employed equally as well in the production of racemic mixtures as in the preparation of optically active isomers. As such, the scope of the present invention extends to this feature as well.

Turning now to the individual steps of the novel process of the present invention, it is noted that step (a), which provides novel N-tert-butoxycarbonyl derivatives of formula (III) above, proceeds by reacting a starting material of formula (II) with a reagent capable of forming the N-tert-butoxycarbonyl derivative thereof. Such reagents are well-known to those skilled in the art of peptide synthesis, where they are widely used to protect the amino group of amino acids. Typical reagents include t-butylazidoformate, di(t-butyl)dicarbonate and the like, with t-butylazidoformate being a preferred reagent. Obviously, the choice of solvent and other reaction conditions will depend upon the particular reagent employed, suitable solvents and conditions being apparent to those skilled in the art of peptide synthesis. In the case of t-butylazidoformate, the reaction can be conveniently conducted in pyridine, preferably in the presence of triethylamine, although a dioxane/magnesium oxide solvent system may be employed in place of the pyridine/triethylamine. Time and temperature depend on the particular starting material of formula (II), the particular reagent and the particular solvent system employed. Generally speaking, heating accelerates the reaction, which is typically complete in 16 hours or less at a temperature of 40°–90° C. The reaction is conveniently conducted at atmospheric pressure, preferably under nitrogen.

With respect to step (b) of the instant process, i.e. reacting a novel N-tert-butoxycarbonyl derivative of formula (III) with an acyloxymethyl chloride of formula (IV), it is to be noted that this reaction is surprising in two respects, namely: (1) that the phenolic hydroxy group(s) of the compound of formula (III) react to form the corresponding ester group(s), not the acyloxymethyl ether group(s) as would normally be expected; and (2) that the stereochemical integrity of the starting material is maintained during the acylation. The reaction is conducted in an organic solvent in the presence of a base. Suitable base/solvent combinations are those which are known to neutralize phenolic hydroxy groups without causing undesirable side reactions such as oxidation. Choice of particular solvent and base will depend upon the nature of the starting material of formula (III). For example, in the case of catechol amines, e.g. derivatives of epinephrine, a potassium carbonate/acetone combination has been found to be highly desirable. On the other hand, when the starting material of formula (III) is not a catechol, e.g. a 3,5-dihydroxyphenol or a monohydroxyphenol, then a stronger base such as potassium carbonate may be used in an appropriate solvent, e.g. methanol. Time, temperature and pressure are not critical factors. The reaction is conveniently conducted at atmospheric pressure, under nitrogen. Time and temperature vary with the particular starting materials employed. Typical reaction times are 30 minutes to 4 days, while typical temperatures are from room temperature to reflux.

With respect to step (c) of the process of the present invention, i.e. removal of the amino protecting group from the compound of formula (V), it is to be noted that this reaction is analogous to those well-known in the art of peptide synthesis. Thus, removal of the protecting group can be achieved by any means suitable for removing a tert-butoxy-carbonyl group without affecting the remaining portions of the molecule, for example, by use of trifluoroacetic acid in dichloromethane, or hydrogen chloride in ethyl acetate, at room temperature or, preferably, below room temperature, for a short period of time (e.g. 15 minutes to 2 hours). The use of HCl in ethyl acetate is a preferred means of removing the protecting group, since it affords the compound of formula (I) in the form of its highly desirable hydrochloride salt. However, the salt formed by the acid which is used to remove the protecting group can be readily neutralized to the free base of formula (I) and then, if desired, reacted with an appropriate acid to form the corresponding nontoxic, pharmaceutically acceptable acid addition salt. Alternatively, the salt obtained after removal of the protecting group, e.g. the hydrochloride, can be subjected to an ion exchange procedure in order to obtain a different, nontoxic, pharmaceutically acceptable salt of formula (I).

Without further elaboration, it is believed that one of ordinary skill in the art can, using the preceding description, utilize the present invention to its fullest extent. Consequently, the following preferred specific embodiments are to be construed as merely illustrative and not limitative of the remainder of the specification and claims in any way whatsoever.

EXAMPLE 1

Preparation of R-3,4-Dihydroxy-α-[(N-methyl-N-tert-butoxycarbonyl)aminomethyl]benzyl alcohol 18.3 G (0.10 mole) of R-(−)-epinephrine and 14.3 g (0.10 mole) of t-butylazidoformate [L. A. Carpino et al, *Organic Synthesis,* Collective Vol. 5, H. E. Baumgarten, ed., John Wiley and Sons, New York, p. 157 (1973)] were combined with 13.9 ml (0.1 mole) of triethylamine in 25 ml of pyridine. The reaction mixture was stirred under nitrogen at 60° C. for approximately 16 hours. The solvent was evaporated from the resultant solution and the residue was taken up in 200 ml of ether. The ether solution was washed successively with 10% hydrochloric acid, saturated sodium bicarbonate solution, water, and saturated sodium chloride solution, then was dried over magnesium sulfate and evaporated to give 14.6 g of a reddish brown glass. IR (CHCl$_3$): 3540 (free OH), 3360 (OH), 1660 cm$^{-1}$

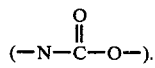

NMR (CDCl$_3$TMS): δ1.40 (s, 9H, C(CH$_3$)$_3$), 2.73 (s, 3H, NCH$_3$), 3.33 (broad s, 2H, —CH$_2$N), 4.70 (broad s, 1H, CH—OH), 6.70 (broad s, 2H, aromatic), 6.80 (broad s, 1H, aromatic).

Similarly prepared from dl-epinephrine, dl-isoproterenol, l-isoproterenol, l-norepinephrine, l-phenylephrine, l-metaraminol, dl-metaproterenol and dl-terbutaline are the t-butoxycarbonyl derivatives thereof, namely dl-3,4-dihydroxy-α-[(N-methyl-N-tert-butoxycarbonyl)aminomethyl]benzyl alcohol; dl-3,4-dihydroxy-α-[(N-isopropyl-N-tert-butoxycarbonyl)aminomethyl]benzyl alcohol; l-3,4-dihydroxy-α-[(N-isopropyl-N-tert-butoxycarbonyl)aminomethyl]benzyl alcohol; l-α-[(N-tert-butoxycarbonyl)aminomethyl]-3,4-dihydroxybenzyl alcohol; l-m-hydroxy-α-[(N-methyl-N-tert-butoxycarbonyl)aminomethyl]benzyl alcohol; l-α-[1-(N-tert-butoxycarbonyl)aminoethyl]-m-hydroxybenzyl alcohol; dl-3,5-dihydroxy-α-[(N-isopropyl-N-tert-butoxycarbonyl)-aminomethyl]benzyl alcohol; and dl-α-[(N-tert-butyl-N-tert-butoxycarbonyl)aminomethyl]-3,5-dihydroxybenzyl alcohol, respectively.

EXAMPLE 2

Preparation of R-α-[(N-Methyl-N-tert-butoxycarbonyl)aminomethyl]benzyl alcohol 3,4-dipivalate To 100 ml of dry acetone were added 2.6 g (0.0095 mole) of R-3,4-dihydroxy-α-[(N-methyl-N-tert-butoxycarbonyl)-aminomethyl]benzyl alcohol, 14.3 g (0.095 mole) of chloromethyl pivalate, and 2.6 g (0.0095 mole) of potassium carbonate. The reaction mixture was stirred overnight, then filtered. The filtrate was evaporated to dryness and the resulting oil was dissolved in a small amount of petroleum ether (b.p. 30°–60° C.). That solution was then chromatographed on a silica gel column. Elution with 2 column volumes of petroleum ether (b.p. 30°–60° C.) gave 7.0 g of recovered chloromethyl pivalate. The desired crude product was obtained by elution with 2 column volumes of ethyl acetate, followed by evaporation of solvent. The crude material was rechromatographed on silica gel and eluted with chloroform to give a pale yellow oil which crystallized upon standing. That solid was recrystallized from petroleum ether (b.p. 30°–60° C.) to give 1.9 g of product, mp 103°–105° C. Analysis: Cal'd for C$_{24}$H$_{37}$NO$_7$: C, 63.83; H, 8.26; N, 3.10. Found: C, 63.95; H, 8.50; N, 2.99.

In a similar manner, the t-butoxycarbonyl derivatives of dl-epinephrine, dl-isoproterenol, l-isoproterenol, l-norepinephrine, l-phenylephrine, l-metaraminol, dl-metaproterenol and dl-terbutaline are reacted with chloromethyl pivalate to afford the corresponding t-butoxycarbonyl pivalates and dipivalates, i.e., dl-α-[(N-methyl-N-tert-butoxycarbonyl)-aminomethyl]benzyl alcohol 3,4-dipivalate; dl-α-[(N-isopropyl-N-tert-butoxycarbonyl)aminomethyl]benzyl alcohol 3,4-dipivalate; l-α-[(N-isopropyl-N-tert-butoxycarbonyl)aminomethyl]-benzyl alcohol 3,4-dipivalate; l-α-[(N-tert-butoxycarbonyl)-aminomethyl]benzyl alcohol 3,4-dipivalate; l-α-[(N-methyl-N-tert-butoxycarbonyl)aminomethyl]-benzyl alcohol 3-pivalate; l-α-[1-(N-tert-butoxycarbonyl)aminoethyl]benzyl alcohol 3-pivalate; dl-α-[(N-isopropyl-N-tert-butoxycarbonyl)aminomethyl]benzyl alcohol 3,5-dipivalate; and dl-α-[(N-tert-butyl-N-tert-butoxycarbonyl)aminomethyl]benzyl alcohol 3,5-dipivalate, respectively.

EXAMPLE 3

Preparation of R-(−)-α-[(Methylamino)methyl]benzyl alcohol 3,4-dipivalate hydrochloride A solution of 400 mg of R-α-[(N-methyl-N-tert-butoxycarbonyl)aminomethyl]benzyl alcohol 3,4-dipivalate in 10 ml of ethyl acetate was cooled to 4° C. in an ice bath and dry nitrogen was bubbled into the solution. After cooling, hydrogen chloride gas was bubbled into the solution until thin layer chromatography indicated that no unreacted starting material remained (approximately 1 hour). Solvent was removed from the reaction mixture to give a white foam. That residue was crystallized from a 1:1 mixture of acetone and hexane to afford 300 mg of white crystals, m.p. 155°–157° C., [α]$_D^{25}$ = −27.4 (C=1.25, H$_2$O). Analysis: Cal'd for C$_{19}$H$_{30}$ClNO$_5$: C, 58.83; H, 7.80; N, 3.61. Found: C, 58.50; H, 7.95; N, 3.36.

In a similar manner, substitution of the products named in the second paragraph of Example 2 in the procedure detailed above, or its obvious chemical equivalent, affords the following products: dl-α-[(methylamino)methyl]benzyl alcohol 3,4-dipivalate hydrochloride; dl-α-[(isopropylamino)methyl]benzyl alcohol 3,4-dipivalate hydrochloride; l-α-[(isopropylamino)methyl]benzyl alcohol 3,4-dipivalate hydrochloride; l-α-(aminomethyl)benzyl alcohol 3,4-dipivalate hydrochloride; l-α-[(methylamino)methyl]benzyl alcohol 3-pivalate hydrochloride; l-α-(1-aminoethyl)benzyl alcohol 3-pivalate; dl-α-[(isopropylamino)methyl]benzyl alcohol 3,5-dipivalate; and dl-α-[(tert-butylamino)methyl]benzyl alcohol 3,5-dipivalate, respectively.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What I claim is:

1. A compound of the general formula

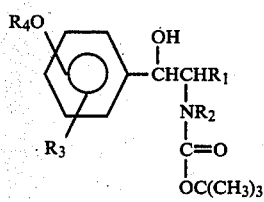

wherein $R_1$ is H or alkyl of 1 to 7 carbon atoms; $R_2$ is H, alkyl of 1 to 7 carbon atoms, or

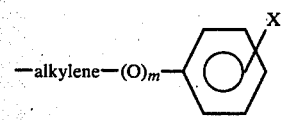

wherein m is zero or one, the alkylene portion contains 1 to 5 carbon atoms, and X is H or $-OR_4'$ wherein $R_4'$ is identical to $R_4$ as defined below; $R_3$ is H, Cl, $-CH_2OH$ or $-OR_4''$ wherein $R_4''$ is identical to $R_4$ as defined below; and $R_4$ is an acyl radical.

2. A compound of claim 1 wherein $R_1$ is hydrogen.

3. A compound of claim 1 wherein $R_1$ is methyl or ethyl.

4. A compound of claim 1 wherein $R_2$ is hydrogen.

5. A compound of claim 1 wherein $R_2$ is alkyl of 1 to 7 carbon atoms.

6. A compound of claim 1 wherein $R_2$ is methyl, isopropyl or tert-butyl.

7. A compound of claim 1 wherein $R_2$ is

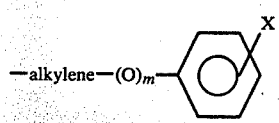

wherein alkylene, m and X are as defined in claim 1.

8. A compound of claim 7 wherein alkylene is ethylene, 1,2-propylene or 1,3-butylene.

9. A compound of claim 1 wherein $R_3$ is hydrogen.

10. A compound of claim 1 wherein $R_3$ is $-OR_4''$ wherein $R_4''$ is as defined in claim 1.

11. A compound of claim 1 wherein $R_4$ is an acyl radical selected from the group consisting of alkanoyl having 1 to 22 carbon atoms; alkenoyl having one or two double bonds and having 4 to 22 carbon atoms; cycloalkyl

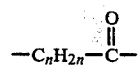

having a total of 4 to 10 carbon atoms of which 3 to 7 are ring carbon atoms in the cycloalkyl portion and wherein n is zero, one or two; phenoxyacetyl; naphthalenecarbonyl; pyridinecarbonyl; and

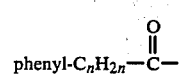

wherein n is zero, one or two and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 1 to 6 carbon atoms.

12. A compound of claim 11 wherein $R_4$ is alkanoyl having 1 to 22 carbon atoms.

13. A compound of claim 12 wherein the alkanoyl radical is branched-chain.

14. A compound of claim 13 wherein the branched-chain alkanoyl radical is pivaloyl.

15. A compound of claim 1 which is selected from the group consisting of the N-tert-butoxycarbonyl 3,4-dipivalate derivatives of epinephrine, isoproterenol and norepinephrine.

16. A compound of claim 1 which is R-α-[(N-methyl-N-tert-butoxycarbonyl)aminomethyl]benzyl alcohol 3,4-dipivalate.

17. A compound of claim 1 which is selected from the group consisting of the N-tert-butoxycarbonyl 3-pivalate derivatives of phenylephrine and metaraminol.

18. A compound of claim 1 which is selected from the group consisting of the N-tert-butoxycarbonyl 3,5-dipivalate derivatives of metaproterenol and terbutaline.

* * * * *